United States Patent [19]
Wako et al.

[11] Patent Number: 5,938,589
[45] Date of Patent: Aug. 17, 1999

[54] CONTROL SWITCH DEVICE FOR AN ENDOSCOPE DUCT

[75] Inventors: Fumihide Wako; Haruo Akiba, both of Omiya, Japan

[73] Assignee: Fuji Photo Optical Co., Ltd., Omiya, Japan

[21] Appl. No.: 09/110,216

[22] Filed: Jul. 6, 1998

[30] Foreign Application Priority Data

Jul. 15, 1997 [JP] Japan .................................. 9-207221
Jul. 17, 1997 [JP] Japan .................................. 9-210084

[51] Int. Cl.⁶ ........................................................ A61B 1/00
[52] U.S. Cl. ........................ 600/159; 600/158; 200/1 B; 200/5 B
[58] Field of Search .................................. 600/104, 152, 600/156, 158, 159; 200/1 B, 5 A, 5 B

[56] References Cited

U.S. PATENT DOCUMENTS

| | | | |
|---|---|---|---|
| 2,360,128 | 3/1944 | Hausler | 200/1 B |
| 2,489,185 | 2/1949 | Johnson | 200/1 B |
| 2,806,907 | 9/1957 | Mazzola | 200/1 B |
| 3,413,430 | 11/1968 | Sharples | 200/1 B |
| 4,063,054 | 12/1977 | Hirata | 200/1 B |
| 4,095,059 | 6/1978 | Nishioka | 200/5 B |
| 4,122,319 | 10/1978 | Jamet | 200/1 B |
| 4,206,333 | 6/1980 | Savas | 200/1 B |
| 4,524,255 | 6/1985 | Haag | 200/1 B |
| 4,548,197 | 10/1985 | Kinoshita | 600/158 |
| 4,668,843 | 5/1987 | Watanabe | 200/1 B |
| 4,832,473 | 5/1989 | Ueda | 600/152 |
| 4,881,523 | 11/1989 | Heckele | 600/159 |
| 5,115,108 | 5/1992 | Ogawa | 200/1 B |
| 5,159,446 | 10/1992 | Hibino | 600/152 |
| 5,301,636 | 4/1994 | Negoro | 600/159 |
| 5,313,027 | 5/1994 | Inoue | 200/1 B |
| 5,347,992 | 9/1994 | Pearlman | 600/159 |
| 5,717,176 | 2/1998 | Dahlstrom | 200/1 B |
| 5,725,478 | 3/1998 | Saad | 600/158 |

*Primary Examiner*—Jeffrey A. Smith
*Assistant Examiner*—Ira Hatton
*Attorney, Agent, or Firm*—Ronald R. Snider

[57] ABSTRACT

The present invention provides a control switch device in which in an endoscope using an electrical control switch to carry out duct control, the conventional operation sense is left, and the flow rate in a duct can be regulated securely. An air/water feed switch portion disposed in an endoscope control section is configured so that a push button, first piston body, and second piston body are moved vertically by using a spring member in an upper and lower support cylinders. The second piston body is operated with an operation stroke which is longer than the stroke of the first piston body, and both of these piston bodies turn on/off an air feed switch and a water feed switch. Also, a suction switch using a pressure-sensitive sensor is used, and this suction switch is turned on/off by the piston body. At this time, in the suction switch, the operation pressure of the push button is detected, and suction of flow rate according to the operation pressure is effected. Also, a plurality of piston bodies capable of being moved vertically with an operation stroke may be provided, and the corresponding switches may be pushed sequentially by these plural piston bodies to variably control the flow rate.

5 Claims, 6 Drawing Sheets

(AIR FEED OPERATION IS ON)

(WATER FEED OPERATION IS ON)

6
CONTROL SWITCH DEVICE FOR AN ENDOSCOPE DUCT

BACKGROUND OF THE INVENTION

This application claims the priority of Japanese Patent Applications No. 9-207221 filed on Jul. 15, 1997, and No. 9-210084 filed on Jul. 17, 1997, which are incorporated herein by reference.

1. Field of the Invention

The present invention relates to a control switch device for an endoscope duct and, more particularly, to a construction of a control switch device for carrying out the opening/closing control and flow rate control of a duct such as an air/water feed duct and suction duct provided in an endoscope.

2. Description of the Prior Art

An endoscope device is provided with, for example, a CCD (Charge Coupled Device), which is an image pick-up device, at the distal end thereof to pick up an image of the interior of body being observed, which is irradiated via a light guide, for observation, and also can feed air and water to an observation window etc. at the distal end or suck the content in the body being observed. Specifically, in the endoscope, an air feed duct and water feed duct connected to air/water feed means are disposed, and a suction duct, which is connected to suction means and used also as a treatment tool insertion channel, is disposed. As a control valve device (mechanical opening/closing valve) for these ducts, there is provided a control section in which an air/water feed valve and a suction valve are integrated with the endoscope.

According to the operation of the aforesaid air/water feed valve, for example, air is fed by opening the air feed duct at the time of a first-stage pushing operation, and water is fed by closing the air feed duct and opening the water feed duct at the time of a second-stage pushing operation. Also, the suction duct is opened by the pushing operation of the suction valve so that filth and the like in the body being observed can be sucked.

BRIEF SUMMARY OF THE INVENTION

Object of the Invention

In recent years, an endoscope device has been proposed in which the valve opening/closing function, which has been performed by the air/water feed valve and suction valve, is not arranged in the endoscope control section, but is arranged in, for example, an electromagnetic valve unit, which is separate from the endoscope serving as a scope. In the endoscope control section, therefore, an electrical control switch, not a mechanical valve type control member, is disposed.

However, this electrical control switch device differs from the conventional valve device in the operation sense. If the operation sense is greatly different from the conventional one, there is inconvenience such that the operation is difficult to perform. Also, when the electrical control switch is used as the control switch for air/water feed etc., different operation of air feed and water feed is performed by the pushing operation of two stages of one operation body. Therefore, when the second operation has a degree of stroke, inadvertent operation can be prevented, and the operation can be made easy to perform.

Further, in the conventional duct control member such as the valve device, the flow rate in the duct (the opening/closing amount of duct) cannot be regulated securely. That is to say, there is a problem in that although some regulation of flow rate can be made by changing the pushing condition of a push button little by little, the fine control of the push button is actually difficult to carry out.

The present invention was made to solve the above problems, and accordingly an object thereof is to provide a control switch device for an endoscope duct in which even when an electrical control switch is used, the conventional operation sense is left to some degree, and the control for opening/closing a duct is carried out easily. Also, another object of the present invention is to provide a control switch device in which in an endoscope using an electrical control switch to carry out duct control, the flow rate in the duct can be regulated securely.

Summary of the Invention

To achieve the above objects, the present invention provides a control switch device for an endoscope duct, comprising: a plurality of switches for giving an operation control signal to an opening/closing valve control section for opening/closing a duct; a first piston body, which is disposed in a support cylinder so as to be movable vertically, for turning on/off one of the plural switches by the operation of a first-stage stroke; and a second piston body, which is disposed in a support cylinder so as to be movable vertically, for turning on/off another one of the plural switches by the operation of a second-stage stroke which is longer than the stroke of the first piston body after the first piston body has stopped.

In this control switch device, it is preferable that the movable portion center of the switch be located at a position shifted from the center of the piston body, and a stop auxiliary member for stabilizing the stopping state of the piston body be disposed at the same height as the pushed-down position of the movable portion.

According to the above configuration, when a push button is pushed lightly, the first piston body is pushed down, and, for example, an air feed switch (electrical switch) is turned on by the tip end face of the first piston body. When the push button is further pushed and the second piston body is moved by a predetermined stroke, for example, a water feed switch (electrical switch) is turned on by the tip end face of the second piston body. The stroke of the second piston body at this time is set to be longer than the stroke of the first piston body, so that the operation is performed with the operation sense of the conventional opening/closing valve, and water feed is not effected inadvertently.

Also, the movable portion center of the switch is shifted from the center of the piston body, and the frame body of, for example, the water feed switch is disposed as the stop auxiliary member of the first piston body for the air feed operation, whereby two switches are arranged in a narrow range, so that the switch device can be configured in a compact manner.

Further, the control switch device for an endoscope duct in accordance with another invention comprises: a piston body disposed so as to be moved vertically by a predetermined operation stroke in a support cylinder by the push of a push button; and an operation state detecting switch which is turned on/off by the piston body and outputs a control signal corresponding to a manipulated variable (operation pressure, operation stroke, etc.) of the push button at the on-time, and is characterized in that the control switch device is configured so that the control signal from the operation state detecting switch is supplied to an opening/closing valve control section for the endoscope duct to control the flow rate in the duct.

A pressure-sensitive sensor can be provided as the operation state detecting switch to control the flow rate by the pushing force of the operation.

According to the above-described configuration, the piston body is driven by the pushing operation of the push button. The operation pressure (pushing pressure) of this push button is detected by, for example, the pressure-sensitive sensor, and a control signal formed on the basis of this detection is output to the opening/closing valve control section. That is, the detection signal of this pressure-sensitive sensor is a signal of pressure value, and this signal of pressure value is supplied to the opening/closing valve control section as a control signal of, for example, three stages (this opening/closing valve control section may recognize the signal of pressure value as a three-stage control signal). Thereupon, in the opening/closing valve control section, the opening/closing of duct or the drive of pump is controlled so that the flow rate is of three stages. As a result, the flow rate etc. in, for example, a suction duct are controlled with intensity of three stages.

Also, as the operation state detecting switch, a plurality of piston bodies are moved vertically with a different operation stroke, and a plurality of switches can be turned on sequentially. In this case, the flow rate can be controlled variably by the control signal output in the predetermined order.

DETAILED DESCRIPTION OF THE PREFERRED EMBODIMENTS

First Embodiment

Figure 1:
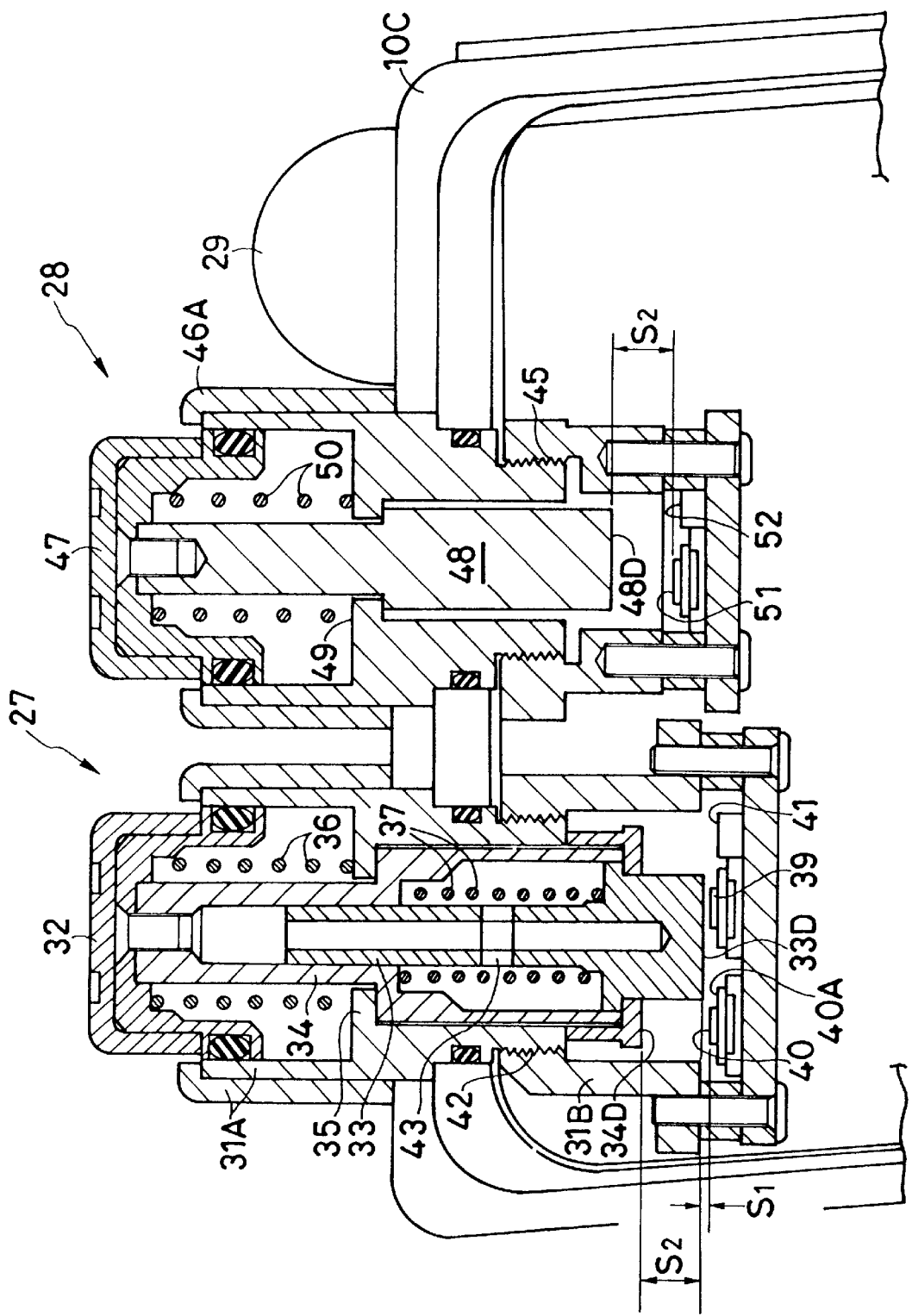
FIG. 1 is a longitudinal sectional view showing a configuration of a control switch device for an endoscope duct in accordance with a first embodiment of the present invention.
Figure 2:
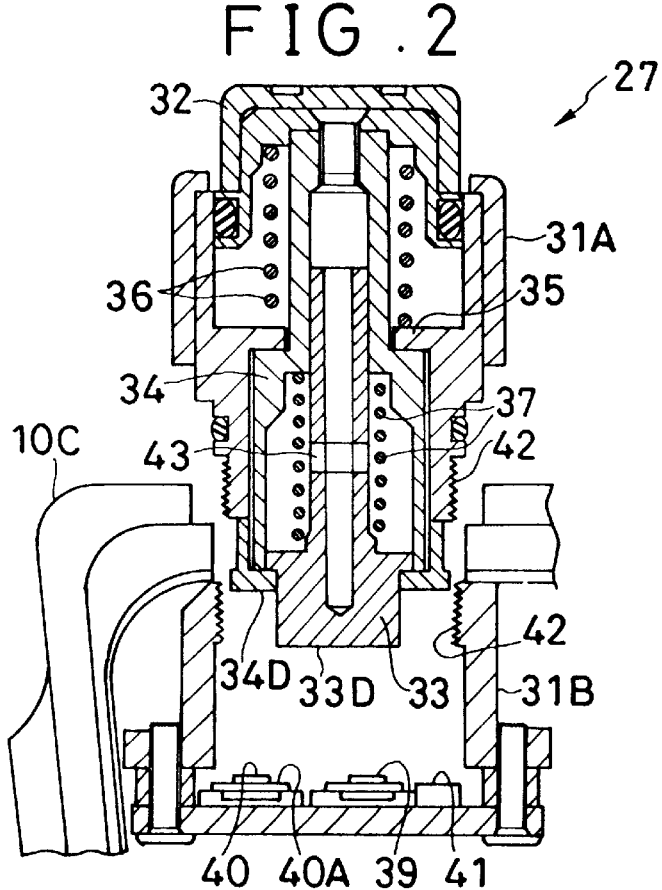
FIG. 2 is a longitudinal sectional view showing a state in which an upper support cylinder of an air/water feed switch section, which is the control switch device in FIG. 1, is separated.
Figure 3:
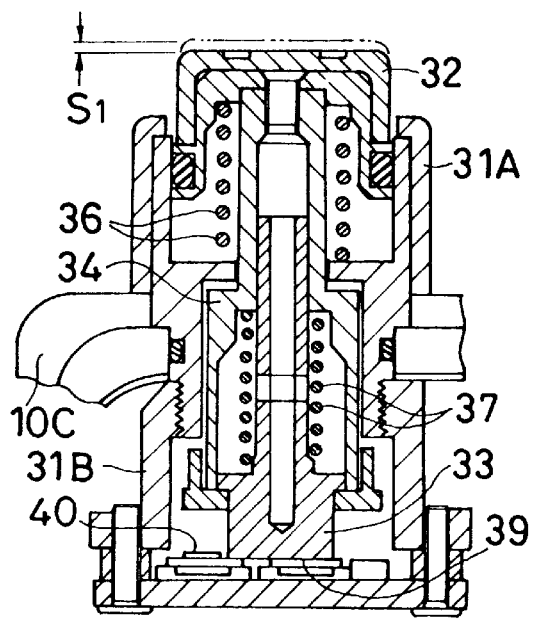
FIG. 3(A) is a view at the time of air feed operation of the air/water feed switch section of the first embodiment.
FIG. 3(B) is a view at the time of water feed operation of the air/water feed switch section of the first embodiment.
Figure 3:
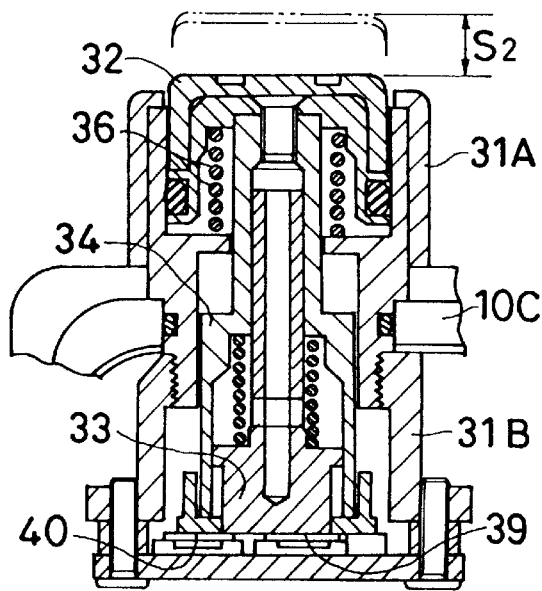
Figure 4:
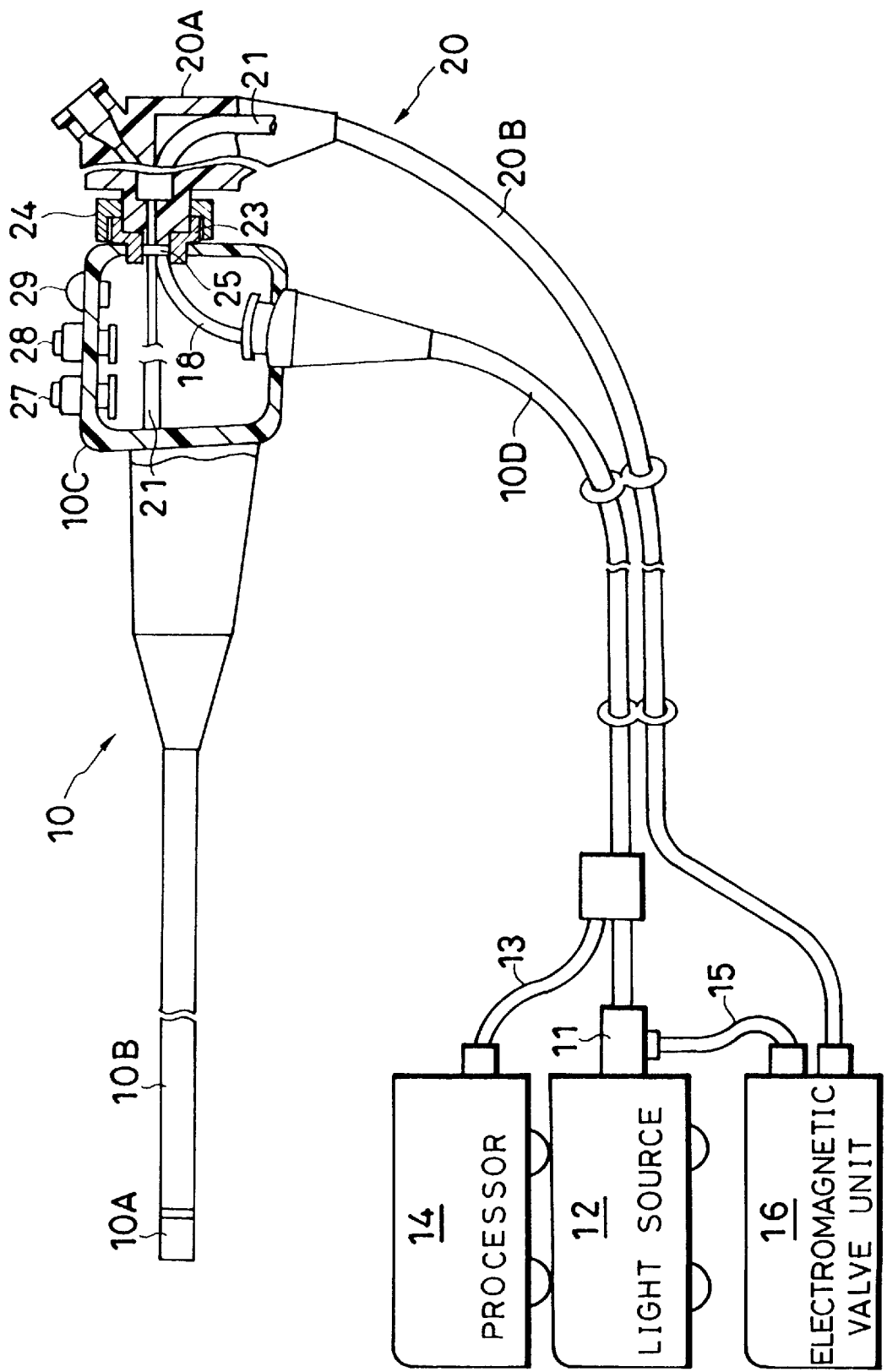
FIG. 4 is a view showing a whole configuration of an endoscope to which the control switch device of this embodiment is applied.

FIGS. 1 to 3 show a control switch device for an endoscope duct in accordance with a first embodiment. FIG. 4 shows the whole view of an electronic endoscope. First, the whole configuration of endoscope will be explained. In FIG. 4, an electronic endoscope 10, which is a scope, includes a distal end portion 10A having a CCD, insertion portion 10B, control section 10C, and first cable 10D. The endoscope 10 is connected to a light source device 12 by a connector 11 of the first cable 10D, and connected to a processor (image processing) device 14 by a signal cable 13. That is to say, in the endoscope 10, the light irradiation from the distal end portion 10A is carried out by a light guide disposed from the distal end portion 10A to the light source device 12, and the control of CCD and the reading of an image signal can be carried out via a signal line disposed from the distal end portion 10A to the processor device 14.

Also, a duct cable 15 branching from the connector 11 is connected to an electromagnetic valve unit (duct control unit) 16, and air/water feed ducts (only a water feed duct 18 is shown in the figure) are disposed in the duct cable 15 and the first cable 10D. The electromagnetic valve unit 16 has an electromagnetic valve and the like for controlling the opening/closing of a pump and duct, and is connected electrically to the processor device 14.

Further, the control section 10C is provided with a duct unit 20 (consisting of a support portion 20A and a second cable 20B) which is detachably attached to the control section 10C. By this duct unit 20, a suction duct 21 is connected to the electromagnetic valve unit 16. Specifically, a cylindrical receiving portion 23 formed with external threads is provided on the rear end surface of the control section 10C, and an operation ring 24 formed with internal threads at the inside periphery thereof is provided on the side of the support portion 20A. By threadedly coupling the operation ring 24 with the receiving portion 23, the duct unit 20 is installed to the control section 10C.

Also, the receiving portion 23 is provided with a folded portion 25 in which the air feed duct and the water feed duct 18 are arranged in an opened state, so that brush cleaning can be performed from the duct opening of the folded portion 25 when the duct unit 20 is removed.

The control section 10C is provided with an air/water feed switch portion (device) 27 for controlling the opening/closing of the air feed duct and the water feed duct 18 and a suction switch portion 28 for controlling the opening/closing of the suction duct 21. An on/off signal of these switch portions 27 and 28 is sent to a control circuit in the electromagnetic valve unit 16. Also, together with the switch portions 27 and 28, an image pick-up button 29 is disposed, and an angle control and the like are provided on the rear side of the control section 10C.

As shown in FIG. 1, the air/water feed switch portion 27 is provided with a push button 32, first piston body 33, and second piston body 34 so as to be movable vertically in an upper support cylinder 31A and lower support cylinder 31B serving as housing bodies. That is, the second piston body 34 is integral with the push button 32, and these elements are urged upward by a ring-form spring member 36 (hatching omitted) disposed between a stopper portion 35 of the second piston body 34 and the ceiling face of the push button 32.

Also, the first piston body 33 is installed in the second piston body 34 so as to be movable vertically, and the first piston body 33 is positionally controlled by the portion (stopper structure) of a tip end face 34D of the second piston body 34, and urged downward by a spring member 37. Under these piston bodies 33 and 34, an air feed switch 39 and water feed switch 40 of, for example, a circular shape, which are electrical switches, are installed at the same height at the bottom of the lower support cylinder 31B. These switches are arranged in such a manner that the movable portion (push-button portion) of the air feed switch 39 is pushed by the first piston body 33, while the movable portion of the water feed switch 40 by the second piston body 34.

A tip end face 33D of the first piston body 33 is disposed slightly apart from the air feed switch 39 by a first-stage stroke S1 (for example, 0.5 mm), while the tip end face 34D of the second piston body 34 is disposed apart from the tip end face 33D of the first piston body 33 by a second-stage stroke S2 (for example, 2 to 3.5 mm) which is longer than the stroke S1. Therefore, the first-stage operation stroke of S1 is set to the first piston body 33, and the second-stage operation stroke of S2 is set to the second piston body 34 after the first piston body 33 has stopped.

Further, the air feed switch 39 is disposed so as to be shifted from the center of the tip end face 33D of the first piston body 33, and the water feed switch 40 is disposed so that a frame body 40A thereof comes into contact with the tip end face 33D. Thereupon, the frame body 40A of the water feed switch 40 functions as a stop auxiliary member for stabilizing the position and state when the air feed switch (movable portion) 39 is pushed by the first piston body 33. Also, for the second piston body 34 as well, a stop auxiliary member 41 is disposed at the same height as that of the frame body 40A. The movable portion of each switch 39, 40 lowers to the position of the frame body 40A at the time of on-operation.

Still further, the upper support cylinder 31A and the lower support cylinder 31B are joined to each other by a threaded portion 42, so that as shown in FIG. 2, the upper support cylinder 31A and the piston bodies 33 and 34 attached thereto can be separated from the lower support cylinder 31B. This configuration offers an advantage that the control switch can be repaired easily. As shown in the figures, the first piston body 33 is formed with a vent hole 43 penetrating from the central cavity to the outside to make the vertical operation smooth.

Meanwhile, the suction switch portion 28 is a one-stage switch. In this switch, a push button 47 and a piston body 48 are disposed integrally and so as to be movable vertically in an upper support cylinder 46A and a lower support cylinder 46B joined to each other by a threaded portion 45. The push button 47 and the piston body 48 are urged upward by a spring member 50 disposed between a stopper portion 49 of the piston body 48 and the ceiling face of the push button 47. At the bottom of the lower support cylinder 46B, an electrical switch 51 as well as a stop auxiliary member 52 is installed. This switch 51 is separated from a tip end face 48D of the piston body 48 by a stroke of S2 as described above.

The first embodiment is configured as described above, and the operation of the air/water feed switch portion 27 is as shown in FIG. 3. More specifically, as shown in FIG. 3(A), when the push button 32 is pushed lightly by the stroke of S1 (about 0.5 mm), the first piston body 33 turns on the air feed switch 39, so that air is fed by the duct opening/closing control of the electromagnetic valve unit 16 shown in FIG. 4. Next, as shown in FIG. 3(B), when the push button 32 is pushed by the stroke of S2 (2 to 3.5 mm), the second piston body 34 turns on the water feed switch 40, whereby water is fed.

According to this air/water feed switch portion 27, the operation for feeding water is executed with the stroke S2 larger than the stroke S1, so that air/water feed can be performed with operation sense similar to that of the conventional mechanical valve type operation member. Moreover, since there is a stroke difference of some degree between the first stage and the second stage, the second-stage water feed operation is not performed inadvertently When the first piston body 33 pushes the air feed switch 39, it also comes into contact with the frame body 40A of the water feed switch 40. Also, when the second piston body 34 pushes the water feed switch 40, it also comes into contact with the stop auxiliary member 41. Therefore, even when each switch 39, 40 is disposed so as to be shifted from the center of the tip end face 33D, 34D of the respective piston body 33, 34, stable switching operation is performed.

Further, in the case of the suction switch portion 28, when the push button 47 is pushed by the stroke of S2, the tip end face 48D of the piston body 48 turns on the switch 51, and suction is effected by the opening/closing control of the electromagnetic valve unit 16. In this case as well, operation sense similar to that of the valve type operation member can be obtained by the stroke S2.

As described above, the first embodiment offers an advantage that even when an electrical control switch is used in the endoscope control section, the conventional operation sense can be left to some degree, and moreover an inadvertent operation by the second piston body is eliminated and the opening/closing operation of duct can be made easy.

Also, since the movable portion center of the switch is shifted from the center of the piston body and the stop auxiliary member is disposed, two switches can be disposed in a narrow range, and the control switch device can be configured in a compact manner.

Second Embodiment

Figure 5:
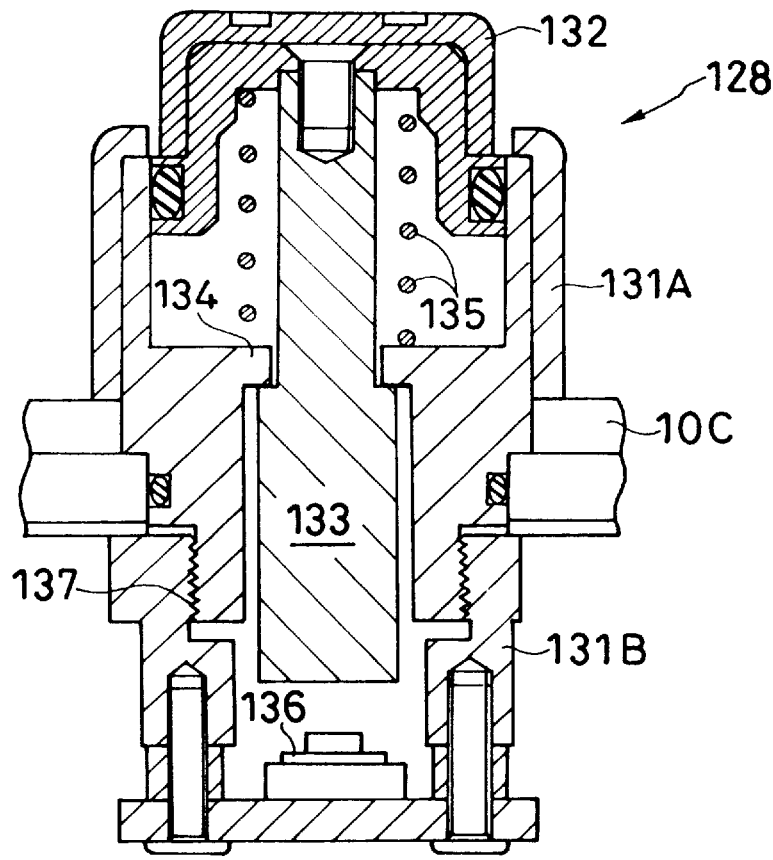
FIG. 5 is a longitudinal sectional view showing a configuration of a control switch device for an endoscope duct in accordance with a second embodiment of the present invention.
Figure 6:
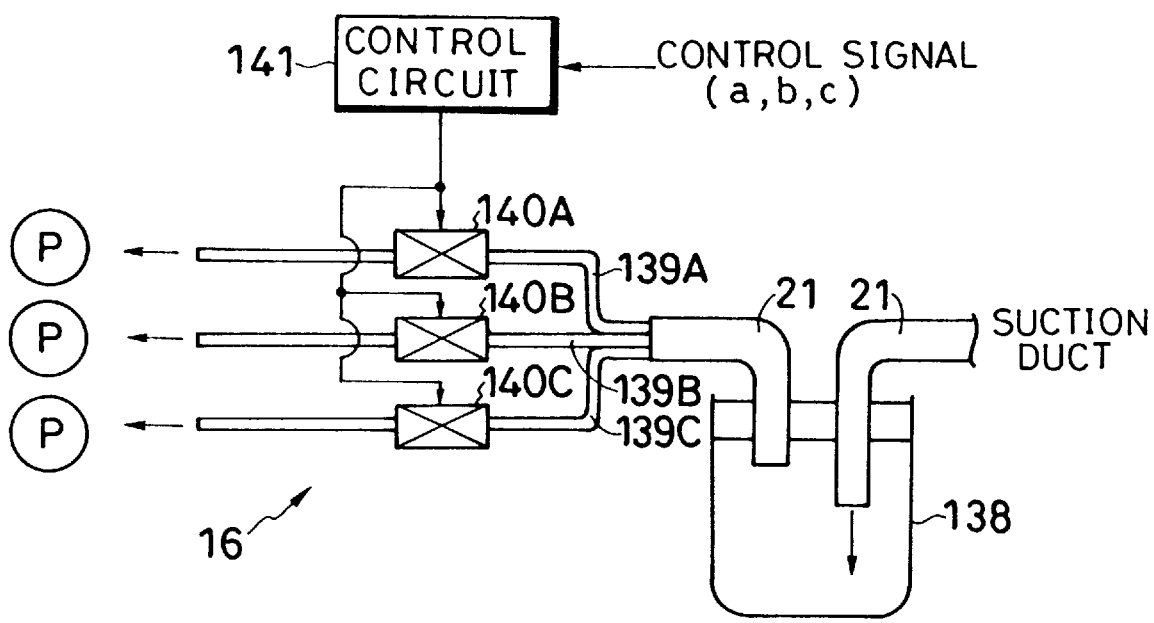
FIG. 6 is a view showing a configuration regarding a suction duct in an electromagnetic valve unit of the second embodiment.

FIGS. 5 and 6 show a control switch device for an endoscope duct in accordance with a second embodiment. This second embodiment is used in place of the suction switch portion 28 of the electronic endoscope 10 explained in FIG. 4.

FIG. 5 shows a configuration of a suction switch portion 128 of the second embodiment. A suction switch portion 128 is provided with a push button 132, and piston body 133 so as to be movable vertically in an upper support cylinder 131A and lower support cylinder 131B serving as housing bodies. That is, the piston body 133 is integral with the push button 132, and these elements are urged upward by a spring member 135 disposed between a stopper portion 134 and the ceiling face of the push button 132.

Also, at the bottom of the lower support cylinder 131B, a suction switch 136 using a pressure-sensitive sensor is installed. This suction switch 136 is disposed so as to be pushed by the tip end face of the piston body 133 by an operation stroke S1 of, for example, 2 to 3.5 mm. That is, this operation stroke S1 is determined so that with reference to a manipulated variable of the conventional mechanical valve device, the operation sense of the valve device is left on the electrical switch device of this embodiment.

This suction switch 136 uses a pressure-sensitive sensor such as a pressure-sensitive diode, pressure-sensitive transistor, or piezo-type micromachine silicon device using the piezoelectric effect. In this embodiment, the push range of the push button 132 is divided into three stages, so that the detection signal of the pressure-sensitive sensor is output as a control signal of three stages.

Further, the upper support cylinder 131A and the lower support cylinder 131B are joined to each other by a threaded portion 137, so that the upper support cylinder 131A and the piston body 133 attached thereto can be separated from the lower support cylinder 131B. Thereupon, the control switch can be repaired easily.

FIG. 6 shows a configuration regarding a suction duct in the aforesaid electromagnetic valve unit 16. As shown in the figure, the suction duct 21 is connected via a sucked object recovery tank 138. This suction duct 21 is connected with three branch ducts 139A, 139B and 139C. These branch ducts 139A, 139B and 139C each are provided with electromagnetic valves 140A, 140B and 140C such as pinch valves, respectively, and a control circuit 141 is disposed. This control circuit 141 operates the electromagnetic valves 140A, 140B and 140C, whereby the opening and closing of the branch ducts 139A, 139B and 139C are controlled. The branch ducts 139A, 139B and 139C each are connected with a suction pump.

The second embodiment is configured as described above, and according to the suction switch portion 128 shown in FIG. 5, when the push button 132 is pushed by the stroke of S1 (2 to 3.5 mm), the piston body 133 turns on the suction switch 36. At the same time, for this suction switch 136, the operation pressure (pushing pressure) of the push button 132 is detected, and a control signal of three stages (for example, a, b and c) corresponding to the magnitude of the operation pressure is supplied to the control circuit 141 of the electromagnetic valve unit 16 shown in FIG. 6. For example, the electromagnetic valve 140A is opened by the a signal, the electromagnetic valve 140B by the b signal, and the electromagnetic valve 140C by the c signal, so that with the increase in the operation pressure of the push button 132, the suction force by the suction duct 21 increases. Therefore, the content in the body being observed can be sucked with a different suction force, that is, a different flow rate.

Third Embodiment

Figure 7:
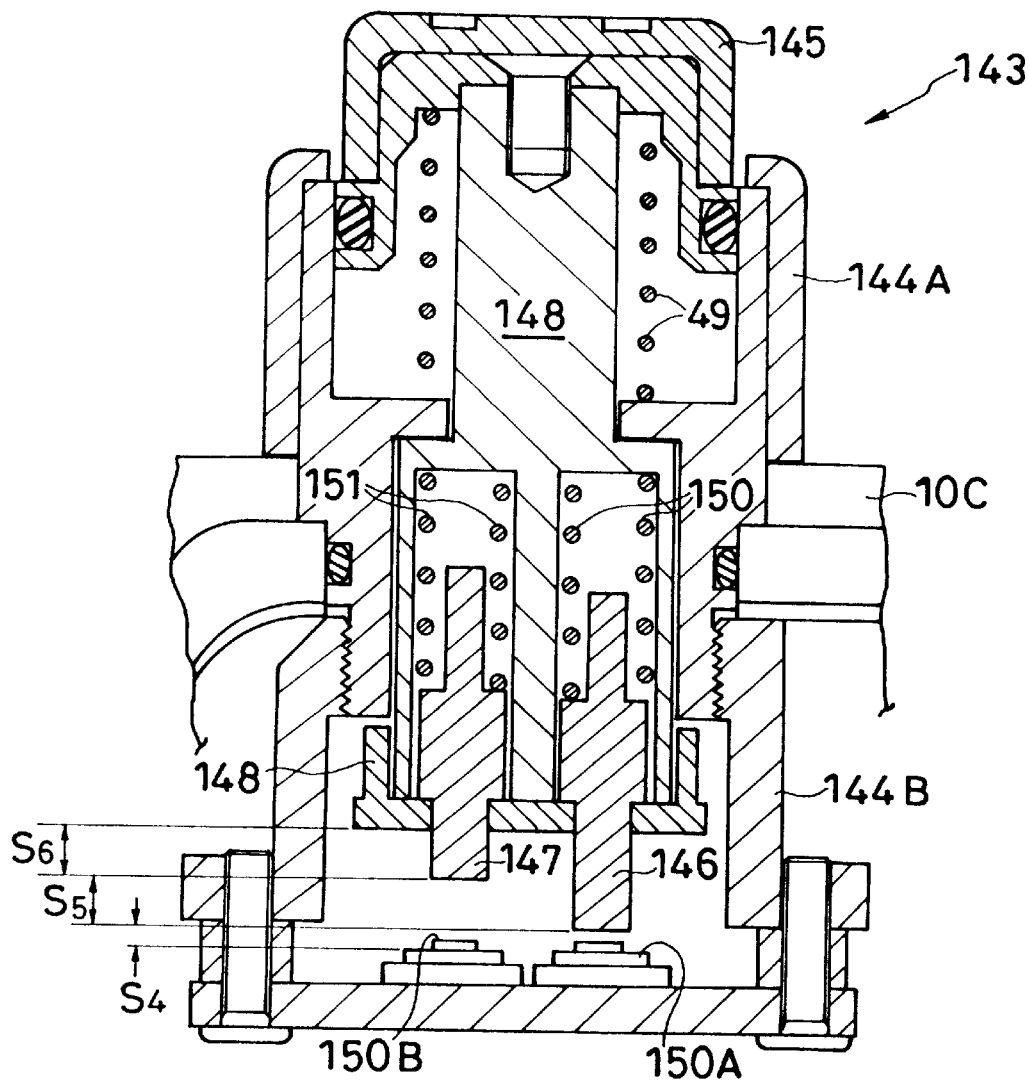
FIG. 7 is a sectional view showing a configuration of a control switch device in accordance with a third embodiment.
Figure 8:
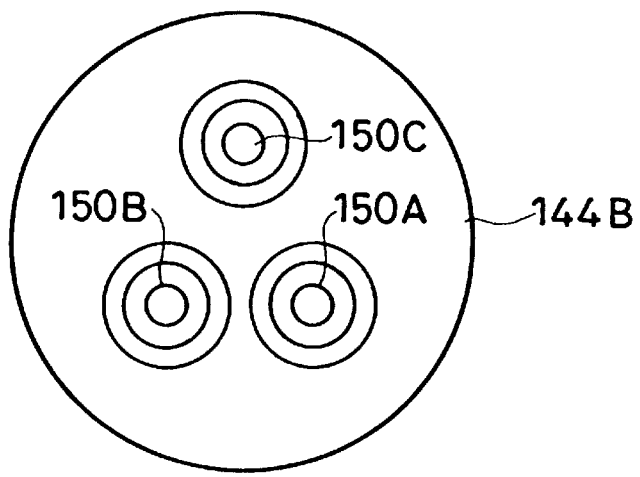
FIG. 8 is a view showing a switch arrangement in a lower support cylinder of the third embodiment.

FIGS. 7 to 9 show a configuration of a suction switch portion of a third embodiment. This third embodiment is so configured that a stepwise control signal is output by the stroke amount. Referring to FIG. 7, a suction switch portion 143 is provided with a push button 145 and first to third piston bodies 146, 147 and 148 so as to be movable vertically in an upper support cylinder 144A and lower support cylinder 144B. That is, the third piston body 148 is integral with the push button 145, and these elements are urged upward by a ring-form spring member 149.

Also, the first piston body 146 and the second piston body 147 are installed in the third piston body 148 so as to be movable vertically, and the first piston body 146 is urged downward by a spring member 150, while the second piston body 147 by a spring member 151. Under these piston bodies 146, 147 and 148, a first-stage suction switch (electrical switch) 150A, a second-stage suction switch 150B, and a third-stage suction switch 150C (FIG. 8) are installed at the same height at the bottom of the lower support cylinder 144B. These suction switches 150A, 150B and 150C perform switching operation by pushing down an uppermost movable portion.

The tip end face of the first piston body 146 is disposed apart from the first-stage suction switch 150A by a short stroke S4 (for example, 0.5 mm), the tip end face of the second piston body 147 is disposed apart from the tip end face of the first piston body 146 by a stroke S5 (several millimeters) which is longer than the stroke S4, and the tip end face of the third piston body 148 is disposed apart from the tip end face of the second piston body 147 by a stroke S6 (for example, S6=S5). Therefore, the first-stage operation stroke of S4 is set to the first piston body 146, the second-stage operation stroke of S5 after the first piston body 146 has stopped is set to the second piston body 147, and the third-stage operation stroke of S6 after the second piston body 147 has stopped is set to the third piston body 148.

Figure 9A:
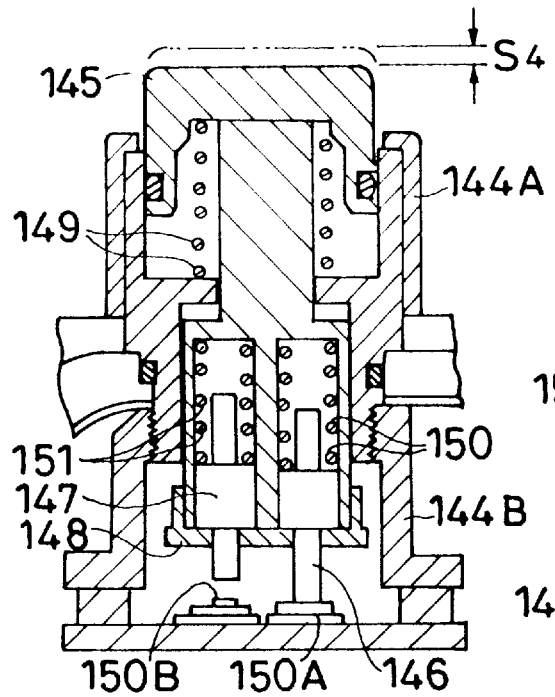
FIG. 9(A) is a view showing a state at the time of the first-stage operation of the control switch device of the third embodiment.
Figure 9B:
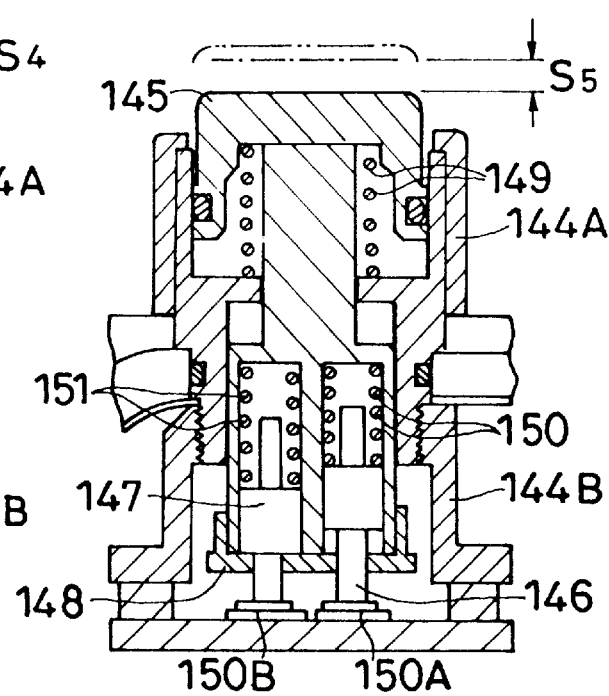
FIG. 9(B) is a view showing a state at the time of the second-stage operation of the switch device shown in FIG. 9(A)
Figure 9C:
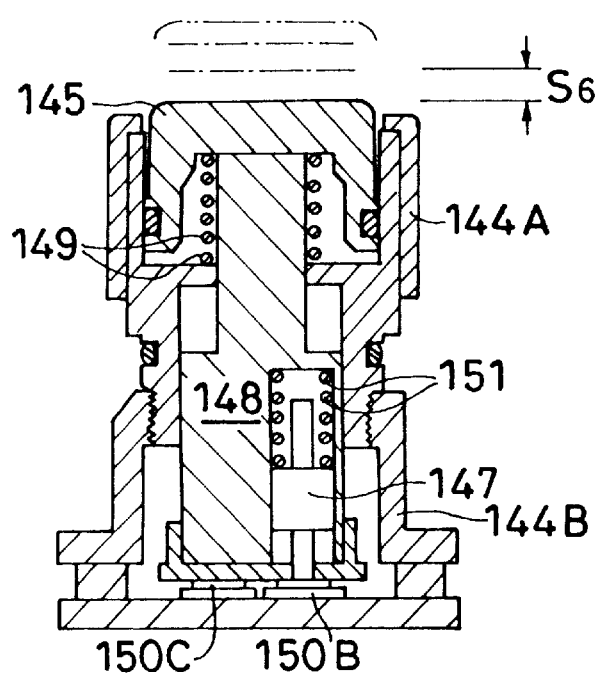
FIG. 9(C) is a view showing a state at the time of the third-stage operation of the switch device shown in FIG. 9(A), the view being turned 90 degrees from the state of FIG. 9((B).

The third embodiment is configured as described above, and the suction switch portion 143 operates as shown in FIGS. 9(A) to 9(C). Specifically, as shown in FIG. 9(A), when the push button 145 is pushed lightly by the stroke of S4, the first piston body 146 turns on the first-stage suction switch 150A (a signal). Then, in the electromagnetic valve unit 16 shown in FIG. 6, the electromagnetic valve 140A is open by the control circuit 141, so that suction is effected by a relatively small suction force via the suction duct 21.

Next, as shown in FIG. 9(B), when the push button 145 is further pushed by the stroke of S5, the second piston body 147 turns on the second-stage suction switch 150B (b signal). At this time, the electromagnetic valve 140B is opened, so that suction is effected by a medium suction force. Also, as shown in FIG. 9(C), which is turned 90 degrees from the state of FIG. 9(B), when the push button 145 is further pushed by the stroke of S6, the third piston body 148 turns on the third-stage suction switch 150C (c signal). In this case, the electromagnetic valve 140C is opened, so that suction is effected by a largest suction force.

Thus, according to the suction switch portion 143, the switches 150A, 150B and 150C are pushed sequentially according to the length of operation stroke of the push button 145, so that the suction flow rate in the suction duct 21 can be regulated variably.

Although the flow rate control is carried out by the branch ducts 139A, 139B and 139C and the electromagnetic valves 140A, 140B and 140C in the electromagnetic valve unit 16 of the above embodiments, the flow rate control may be carried out by controlling the suction force of the suction pump. Also, the present invention is applicable similarly to the air feed duct and the water feed duct 18 in addition to the suction duct 21.

As described above, the second and third embodiments have an advantage that the flow rate in the duct can surely be regulated variably in an endoscope using an electrical control switch.

What is claimed is:

1. A control switch device for an endoscope duct, comprising:

a plurality of switches for giving an operation control signal to an opening/closing valve control section for opening/closing a duct;

a first piston body, which is disposed in a support cylinder so as to be movable vertically, for turning on/off one of said plural switches by the operation of a first-stage stroke; and a second piston body, which is disposed in a support cylinder so as to be movable vertically, for turning on/off another one of said plural switches by the operation of a second-stage stroke which is longer than the stroke of said first piston body after said first piston body has stopped.

2. A control switch device for an endoscope duct according to claim 1, wherein the movable portion center of said switch is located at a position shifted from the center of said piston body, and a stop auxiliary member for stabilizing the stopping state of said piston body is disposed at the same height as the pushed-down position of the movable portion.

3. A control switch device for an endoscope duct, comprising:

a piston body disposed so as to be moved vertically by a predetermined operation stroke in a support cylinder by the push of a push button; and an operation state detecting switch which is turned on/off by said piston body and outputs a control signal corresponding to a manipulated variable of said push button at the on-time;

said control switch device being configured so that the control signal from said operation state detecting switch is supplied to an opening/closing valve control section for the endoscope duct to control the flow rate in the duct.

4. A control switch device for an endoscope duct according to claim 3, wherein a pressure-sensitive sensor is provided as said operation state detecting switch to control the flow rate by the pushing force of the operation.

5. A control switch device for an endoscope duct according to claim 3, wherein as said operation state detecting switch, there are provided a plurality of piston bodies arranged so as to be movable vertically with a different operation stroke in said support cylinder and a plurality of switches turned on/off sequentially by said plural piston bodies, so that the flow rate is controlled by the amount of said operation stroke.

* * * * *